United States Patent [19]

Erpenbach et al.

[11] 4,414,160

[45] Nov. 8, 1983

[54] PROCESS FOR MAKING CARBOXYLIC ACID HALIDES

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 301,984

[22] Filed: Sep. 14, 1981

[30] Foreign Application Priority Data

Sep. 18, 1980 [DE] Fed. Rep. of Germany ....... 3035201

[51] Int. Cl.³ ........................................ C07C 51/58
[52] U.S. Cl. ............................... 260/544 A; 252/428; 252/429 R; 252/431 P; 502/162; 502/154; 502/155
[58] Field of Search .................... 260/544 A; 560/207, 560/236; 562/406, 520

[56] References Cited

U.S. PATENT DOCUMENTS

| | | | |
|---|---|---|---|
| 2,053,233 | 9/1936 | Woodhouse | 260/544 A |
| 3,452,090 | 6/1969 | Mador et al. | 260/544 A |
| 3,454,632 | 7/1969 | Mador et al. | 260/544 A |
| 3,637,833 | 1/1972 | Fenton | 562/406 |
| 3,641,074 | 2/1972 | Fenton | 562/406 |
| 3,769,324 | 10/1973 | Paulik et al. | 562/406 |
| 3,772,380 | 11/1973 | Paulik et al. | 562/520 |
| 3,845,121 | 10/1974 | Eubanks et al. | 260/544 A |

OTHER PUBLICATIONS

Fieser et al, Organische Chemie, Verlag Chemie GmbH, Weinheim/Ber., 1965, p. 474 Houben–Weyl, Methoden der Organischen Chemie, vol. 71 (1954), pp. 285–291.
Forster et al, Catal. Rev. -Sci. Eng. 23:89–105 (1981).
Roth et al, Chem. Tech., Oct. 1971, pp. 600–605.

*Primary Examiner*—Natalie Trousof
*Assistant Examiner*—L. Hendriksen
*Attorney, Agent, or Firm*—Connolly and Hutz

[57] ABSTRACT

The invention relates to the manufacture of carboxylic acid halides. To this end, an alkyl halide having from 1 to 6 carbon atoms or an aryl halide is reacted with carbon monoxide under practically anhydrous conditions at temperatures of 350 to 575 K. and under pressures of 1 to 300 bars in the presence of a catalyst system containing at least one of the noble metals selected from rhodium, palladium, iridium or their compounds, iodine and/or its compounds, methyl trialkyl phosphonium iodide and/or methyl triaryl phosphonium iodide, and optionally trialkyl phosphine oxide or triaryl phosphine oxide as well as an inert organic solvent. More specifically, the reaction mixture is admixed with 0.02 to 0.75 mol of hydrogen per mol of carbon monoxide.

5 Claims, No Drawings

PROCESS FOR MAKING CARBOXYLIC ACID HALIDES

The present invention relates to a process for making carboxylic acid halides by reacting an alkyl halide having from 1 to 6 carbon atoms or an aryl halide with carbon monoxide under practically anhydrous conditions at temperatures of 350 to 575 K. and under pressure of 1 to 300 bars in the presence of a catalyst system containing at least one of the noble metals selected from rhodium, palladium, iridium or their compounds, iodine and/or its compounds, methyl trialkyl phosphonium iodide and/or methyl triaryl phosphonium iodide, and optionally trialkyl phosphine oxide or triaryl phosphine oxide as well as an inert organic solvent, which comprises admixing the reaction mixture with 0.02 to 0.75 mol of hydrogen per mol of carbon monoxide.

It is preferable for the process to be carried out in the presence of a catalyst system which additionally contains one or more compounds of the base metals selected from Ce, Ti, Zr, Hf, Ge, Sn, Pb, V, Nb, Ta, As, Sb, Bi, Cr, Mo, W, Mn, Re, Fe, Co and Ni.

Various processes for making acetyl halides from alkyl halides and carbon monoxide in the presence of a catalyst system containing compounds of rhodium or iridium, an iodide, a tertiary phosphine and/or tertiary phosphine oxide in an inert solvent have already been described in Japanese published Specifications 53/46912 (1978), 53/63307 (1978) and 53/63308 (1978). As disclosed therein, it is possible for the catalyst system to contain as additional ingredients phosphinates of the formula $(R)_2P(=O)OR$, phosphoric acid esters of the formula $(RO)_3PO$ or phosphoric acid triamides of the formula $(R_2N)_3PO$, as promoters.

It is more specifically described in working Examples 1 to 8 of Japanese published Specification No. 53/63307 that acetyl chloride is obtained in yields of 11.6 to 47.3 mol %, based on methyl chloride. The space/time yields and catalyst efficiency, respectively, lie between 35 and 150 g acetyl chloride per liter reaction volume per hour and 42 and 173 g acetyl chloride per gram rhodium per hour, respectively.

German patent application No. P 30 16 900.7 filed earlier describes a process for making acetyl chloride by reacting methyl chloride with carbon monoxide under practically anhydrous conditions at temperatures of 350 to 575 K., under pressures of 1 to 300 bars in the presence of a catalyst system containing at least one of the noble metals selected from rhodium, palladium, iridium or their compounds, iodine and/or its compounds, and optionally trialkyl phosphine oxide or triaryl phosphine oxide as well as an inert organic solvent, which comprises effecting the reaction in the presence of a catalyst system containing n-heptane as the inert solvent and methyl trialkyl phosphonium iodide and/or methyl triaryl phosphonium iodide, and at least one compound of chromium, molybdenum or tungsten as additional ingredients.

In this latter process, acetyl chloride is obtained in yields of 43 to 54% of the theoretical, based on methyl chloride. The space/time yields and catalyst efficiency, respectively, vary between 253 and 479 g acetyl chloride per l reaction volume per hour and between 133 and 252 g acetyl chloride per gram rhodium per hour, respectively, depending on the concentration of the catalyst system and the reaction period.

Although the space/time yields and catalyst efficiency compare very favorably with those disclosed in the aforesaid Japanese published Specification, the fact remains that this latter process is also not fully satisfactory inasmuch as the activity of the catalysts used therein has been found gradually to decrease.

The present invention now permits the yield, space/time yield and catalyst efficiency to be further improved and, especially by the addition of hydrogen, the activity of the carbonylation catalysts used for the manufacture of carboxylic acid halides to be maintained practically constant. Catalysts of which the activity had decreased after repeated use in the absence of hydrogen were found, after the addition of even minor proportions of hydrogen to the carbonylation mixture, not only to resume, but even to excel their initial activity which is critically influenced by promoting the catalyst with one or more compounds of the base metals specified hereinabove.

The noble metals selected from rhodium, palladium, and iridium and the base metals specified above should preferably be used in the form of their chlorides (e.g. $RhCl_3.3H_2O$, $CrCl_3.6H_2O$), acetates, carbonyls e.g. $[Re(CO)_5]_2$, or complex compounds, e.g. $Rh(CO)Cl[P(C_6H_5)_3]_2$, $Ir(CO)Cl[P(C_6H_5)_3]_2$, $RhCl[P(C_6H_5)_3]_3$, $[Rh(CO)_2Cl]_2$, $HIr(CO)[P(C_6H_5)_3]_3$, $HRh(CO)[P(C_6H_5)_3]_3$.

The iodine compound which should preferably be used is methyl iodide, but ethyl iodide or hydrogen iodide can also be employed.

The term "alkyl" in trialkyl phosphine oxide and in methyl trialkyl phosphonium iodide preferably stands for methyl, ethyl, propyl and butyl, and the term "aryl" in triaryl phosphine oxide and methyl triaryl phosphonium iodide preferably stands for phenyl.

The catalyst system comprised of noble metal (-compound)/base metal compound/iodine (-compound)/tertiary phosphine oxide/quaternary phosphonium iodide-/organic solvent should preferably be used in a molar ratio of

1:(0-8):(1-100):(0-50):(1-100):(0-500).

It is also preferable to use 0.0001-0.01 mol noble metal (-compound) and up to 0.08 mol compound of the aforesaid base metals, per mol alkyl or aryl halide.

In accordance with this invention, 0.02 to 0.75 mol hydrogen is added to the reaction mixture, per mol carbon peroxide. Higher proportions of hydrogen should suitably not be used inasmuch as an increasing content of hydrogen has been found, at a given total pressure, to effect a decrease in the partial pressure of the carbon monoxide and in this way adversely to affect yield and efficiency.

The reaction of this invention should preferably be carried out under 20 to 180 bars at 150° to 250° C. (423-523 K.) in the presence of an inert solvent, e.g. hexane, heptane, octane, toluene or xylene.

It is possible for the process of this invention to be carried out discontinuously or continuously.

EXAMPLE 1

(a) 1.95 g $RhCl_3.3H_2O$, 7.91 g $CrCl_3.6H_2O$, 3.4 g triphenyl phosphine oxide, 60 g methyl triphenyl phosphonium iodide, 15.8 g methyl iodide, 150.5 g methyl chloride and 150.5 g n-heptane were placed in a corrosion-resistant, stainless steel autoclave. Initially established was a hydrogen partial pressure of 7.5 bars and then a CO-partial pressure of 75 bars (total pressure=82.5 bars). After a reaction period of 35 minutes at 453 K., the reaction product was taken from the autoclave and analyzed. 131 g acetyl chloride was obtained (56% of the theoretical); this corresponded to a space/time yield of 561 g $CH_3COCl$ per liter reaction volume per hour and to a catalyst efficiency of 295 g $CH_3COCl$ per gram rhodium per hour.

(b) (Comparative experiment)

1.95 g $RhCl_3.3H_2O$, 7.91 g $CrCl_3.6H_2O$, 3.4 g triphenyl phosphine oxide, 60 g methyl triphenyl phosphonium iodide, 15.8 g methyl iodide, 150.5 g methyl chloride and 150.5 g n-heptane were placed in a corrosion resistant, stainless steel autoclave and a CO-pressure of 75 bars was established therein. After a reaction period of 35 minutes at 453 K., the reaction product was found to contain 86 g acetyl chloride (36.8% of the theoretical). This corresponded to a space/time yield of 369 g $CH_3COCl$ per liter reaction volume per hour and to a catalyst efficiency of 194 g $CH_3COCl$ per gram rhodium per hour.

EXAMPLE 2

1.95 g $RhCl_3.3H_2O$, 3.4 g triphenyl phosphine oxide, 60 g methyl triphenyl phosphonium iodide, 15.8 g methyl iodide, 150.5 g methyl chloride and 150.5 g toluene were placed in an autoclave. Initially established therein was a hydrogen partial pressure of 7.5 bars and then a CO-partial pressure of 75 bars. After a reaction period of 35 minutes at 453 K., the reaction product was found to contain 115 g (49% of the theoretical) acetyl chloride. This corresponded to a space/time-yield of 493 g $CH_3COCl$ per liter reaction volume per hour and to a catalyst efficiency of 259 g $CH_3COCl$ per g rhodium per hour.

EXAMPLE 3

1.95 g $RhCl_3.3H_2O$, 9.08 g $BiCl_3$, 60 g methyl triphenyl phosphonium iodide, 15.8 g methyl iodide, 150.5 g methyl chloride and 150.5 g n-heptane were placed in an autoclave. Initially established therein was a hydrogen pressure of 5 bars and then a CO-pressure of 75 bars (total pressure=80 bars). After a reaction period of 35 minutes at 453 K., the reaction product was analyzed and found to contain 136.8 g (58.4% of the theoretical) acetyl chloride. This corresponded to a space/time yield of 586 g $CH_3COCl$ per liter reaction volume per hour and to a catalyst efficiency of 309 g $CH_3COCl$ per gram rhodium per hour.

EXAMPLE 4

1.95 g $RhCl_3.3H_2O$, 4.67 g $FeCl_3$, 3.4 g triphenyl phosphine oxide, 60 g methyl triphenyl phosphonium iodide, 15.8 g methyl iodide, 150.5 g methyl chloride and 150.5 g n-heptane were placed in an autoclave. Initially established therein was a hydrogen pressure of 19 bars and then a CO-pressure of 75 bars (total pressure=94 bars). After a reaction period of 35 minutes at 453 K., the reaction product was taken from the autoclave and found to contain 126 g acetyl chloride (54% of the theoretical). This corresponded to a space/time-yield of 540 g $CH_3COCl$ per liter reaction volume per hour and to a catalyst efficiency of 284 g $CH_3COCl$ per gram rhodium per hour.

EXAMPLE 5

1.31 g $PdCl_2$, 3.4 g triphenyl phosphine oxide, 60 g methyl triphenyl phosphonium iodide, 15.8 g methyl iodide, 150.5 g methyl chloride and 150.5 g toluene were placed in an autoclave. Intially established therein was a hydrogen pressure of 5 bars and then a CO-pressure of 75 bars. After a reaction period of 35 minutes at 453 K., the reaction product was analyzed and found to contain 106 g acetyl chloride (45.3% of the theoretical). This corresponded to a space/time-yield of 454 g $CH_3COCl$ per liter reaction volume per hour and a catalyst efficiency of 230 g $CH_3COCl$ per gram palladium per hour.

EXAMPLE 6

1.95 g $RhCl_3.3H_2O$, 8.82 g $[Re(CO)_5]_2$, 8 g methyl tributyl phosphonium iodide, 45 g methyl triphenyl phosphonium iodide, 16 g methyl iodide, 150.5 g methyl chloride and 150.5 g n-heptane were placed in an autoclave. Initially established therein was a hydrogen pressure of 8 bars and then a CO-partial pressure of 75 bars (total pressure=83 bars). After a reaction period of 35 minutes at 453 K., the reaction product was found to contain 147 g acetyl chloride (62.8% of the theoretical). This corresponded to a space/time-yield of 630 g $CH_3COCl$ per liter reaction volume per hour and to a catalyst efficiency of 332 g $CH_3COCl$ per gram rhodium per hour.

EXAMPLE 7

1.95 g $RhCl_3.3H_2O$, 6.5 g $SnCl_2.2H_2O$, 3.4 g triphenyl phosphine oxide, 60 g methyl triphenyl phosphonium iodide, 15.8 g methyl iodide, 150.5 g methyl chloride and 150.5 g n-heptane were placed in an autoclave. Initially established therein was a hydrogen pressure of 5 bars and then a CO pressure of 75 bars. After a reaction period of 35 minutes at 453 K., the reaction product was found to contain 110 g acetyl chloride (47.0% of the theoretical). The space/time yield was 471 g $CH_3COCl$ per liter reaction volume per hour and the catalyst efficiency was 248 g of $CH_3COCl$ per gram rhodium per hour.

EXAMPLE 8

1.95 g $RhCl_3.3H_2O$, 10.7 g $CeCl_3.7H_2O$, 3.4 g triphenyl phosphine oxide, 60 g methyl triphenyl phosphonium iodide, 15.8 g methyl iodide, 150.5 g methyl chloride and 150.5 g n-heptane were placed in an autoclave. Initially established therein was a hydrogen pressure of 2.5 bars and then a CO pressure of 75 bars (total pressure=77.5 bars). After a reaction period of 35 minutes at 453 K., the reaction product was found to contain 103 g acetyl chloride (44.0% of the theoretical). This corresponded to a space/time-yield of 441 g $CH_3COCl$ per liter reaction volume per hour and to a catalyst efficiency of 232 g $CH_3COCl$ per gram rhodium per hour.

EXAMPLE 9

1.95 g $RhCl_3.3H_2O$, 5.46 g $TiCl_4$, 3.4 g triphenyl phosphine oxide, 60 g methyl triphenyl phosphonium iodide, 15.8 g methyl iodide, 150.5 g methyl chloride and 150.5 g n-octane were placed in an autoclave. Initially established therein was a hydrogen pressure of 2 bars and then a CO-pressure of 75 bars. After a reaction period of 35 minutes at 453 K., the reaction product was analyzed and found to contain 133 g acetyl chloride. This corresponded to a yield of 56.7%, based on methyl chloride, to a space/time-yield of 570 g $CH_3COCl$ per liter reaction volume per hour, and to a catalyst efficiency of 300 g $CH_3COCl$ per g rhodium per hour.

EXAMPLE 10

1.95 g RhCl$_3$.3H$_2$O, 5.7 g MnCl$_2$.4H$_2$O, 60 g methyl triphenyl phosphonium iodide, 15.8 g methyl iodide, 150.5 g methyl chloride and 150.5 g n-heptane were placed in a corrosion-resistant, stainless steel autoclave. Initially established therein was a hydrogen pressure of 8 bars and then a CO pressure of 75 bars. After a reaction period of 35 minutes at 453 K., the reaction product was found to contain 134.3 g acetyl chloride (57.4% of the theoretical). This corresponded to a space/time-yield of 576 g CH$_3$COCl per liter reaction volume per hour and to a catalyst efficiency of 303 g CH$_3$COCl per gram rhodium per hour.

EXAMPLE 11

Reaction product was separated from the catalyst of Example 1b, methyl iodide, methyl chloride and n-heptane were placed once again in the autoclave as described in Example 1b, and the catalyst was repeatedly used. After it had been used 20 times, the space/time yield initially of 369 g CH$_3$COCl per liter reaction volume per hour decreased to 245 g CH$_3$COCl per liter reaction volume per hour and the catalyst efficiency initially of 194 g CH$_3$COCl per gram rhodium per hour decreased to 129 g CH$_3$COCl per gram rhodium per hour. The acetyl chloride yield, based on methyl chloride, decreased from initially 36.8% to 24.5% of the theoretical. In all tests, the reaction period was 35 minutes at 453 K. The catalyst of which the efficiency had so decreased, was used once again together with 15.8 g methyl chloride, 150.5 g methyl chloride and 150.5 g n-heptane in the autoclave. Initially established therein was a hydrogen pressure of 8 bars and then a CO pressure of 75 bars. After a reaction period again of 35 minutes at 453 K., the reaction product was found to contain 127 g acetyl chloride (54.4% of the theoretical). This corresponded to a space/time-yield of 544 g CH$_3$COCl per liter reaction volume per hour and to a catalyst efficiency of 286 g CH$_3$COCl per gram rhodium per hour.

EXAMPLE 12

1.95 g RhCl$_3$.3H$_2$O, 7.91 g CrCl$_3$.6H$_2$O, 3.4 g triphenyl phosphine oxide, 60 g methyl triphenyl phosphonium iodide, 15.8 g methyl iodide, 175 g ethyl chloride and 150.5 g n-heptane were placed in an autoclave. Initially established therein was a hydrogen pressure of 10 bars and then a CO pressure of 75 bars. After a reaction period of 7 hours at 463 K., the reaction product was found to contain 19 g propionyl chloride (7.6% of the theoretical). This corresponded to a space/time-yield of 7 g CH$_3$CH$_2$COCl per liter reaction volume per hour and to a catalyst efficiency of 3.6 g CH$_3$CH$_2$COCl per g rhodium per hour.

EXAMPLE 13

1.95 g RhCl$_3$.3H$_2$O, 7.91 g CrCl$_3$.6H$_2$O, 3.4 g triphenyl phosphine oxide, 45 g methyl tributyl phosphonium iodide, 15.8 g methyl iodide and 300 g methyl bromide were placed in an autoclave. Initially established therein was a hydrogen pressure of 10 bars and then a CO pressure of 75 bars. After a reaction period of 35 minutes at 453 K., the reaction product was taken from the autoclave and analyzed. It was found to contain 169.7 g acetyl bromide (43.7% of the theoretical). This corresponded to a space/time-yield of 727 g CH$_3$COBr per liter reaction volume per hour and to a catalyst efficiency of 383 g CH$_3$COBr per g rhodium per hour.

EXAMPLE 14

1.95 g RhCl$_3$.3H$_2$O, 5.7 g MnCl$_2$.4H$_2$O, 60 g methyl tributyl phosphonium iodide, 18 g methyl iodide, 150.5 g methyl chloride and 150 g toluene were placed in an autoclave. Initially established therein was a hydrogen pressure of 50 bars and then a CO pressure of 75 bars. After a reaction period of 35 minutes at 453 K., the reaction product was found to contain 132 g acetyl chloride (56.4% of the theoretical). This corresponded to a space/time-yield of 566 g CH$_3$COCl per liter reaction volume per hour and to a catalyst efficiency of 297 g CH$_3$COCl per gram rhodium per hour.

We claim:

1. In a process for making carboxylic acid halides by reacting an alkyl halide having from 1 to 6 carbon atoms or an aryl halide with carbon monoxide under practically anhydrous conditions at temperatures of 350 to 575 K. and under pressures of 1 to 300 bars in the presence of a catalyst system containing at least one of the noble metals selected from rhodium, palladium, iridium or their compounds, iodine and/or its compounds, methyl trialkyl phosphonium iodide and/or methyl triaryl phosphonium iodide, the improvement which comprises admixing the reaction mixture with 0.02 to 0.75 mol of hydrogen per mol of carbon monoxide.

2. A process as claimed in claim 1, wherein the reaction is effected in the presence of a catalyst system containing one or more compounds of the base metals selected from Ce, Ti, Zr, Hf, Ge, Sn, Pb, V, Nb, Ta, As, Sb, Bi, Cr, Mo, W, Mn, Re, Fe, Co and Ni as additional ingredients.

3. A process as claimed in claim 1 or 2, wherein the process is carried out in the presence of an inert organic solvent.

4. A process as claimed in claim 1 or 2, wherein the catalyst system contains a trialkyl phosphine oxide or triaryl phosphine oxide as well as an inert organic solvent.

5. A process as claimed in claim 1 or 2, wherein the catalyst system optionally contains trialkyl phosphine oxide or triaryl phosphine oxide as well as an inert organic solvent, and the catalyst system comprised of noble metal(-compound)/base metal compound/iodine(-compound)/tertiary phosphine oxide/quaternary phosphonium iodide/organic solvent is used in a molar ratio of

1:(0–8):(1–100):(0–50):(1–100):(0–500).

* * * * *